US00PP19547P2

(12) United States Plant Patent
Shim

(10) Patent No.: US PP19,547 P2
(45) Date of Patent: Dec. 2, 2008

(54) ***HIBISCUS* PLANT NAMED 'ANTONG TWO'**

(50) Latin Name: *Hibiscus syriacus*
Varietal Denomination: Antong Two

(75) Inventor: Kyung-Ku Shim, YongIn (KR)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 11/999,275

(22) Filed: Dec. 4, 2007

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent L Bell
(74) *Attorney, Agent, or Firm*—C. A. Whealy

(57) ABSTRACT

A new and distinct cultivar of *Hibiscus* plant named 'Antong Two', characterized by its compact, upright and outwardly spreading plant habit; freely branching habit; dark green-colored leaves; small long-lasting white-colored flowers with red purple-colored centers and venation; and good garden performance.

1 Drawing Sheet

Botanical Designation: *Hibiscus syriacus*.
Cultivar Denomination: 'Antong Two'.

BACKGROUND OF THE INVENTION

The present invention relates to a new and distinct cultivar of *Hibiscus*, botanically known as *Hibiscus syriacus*, commercially known as Rose-of-Sharon or Althea, and hereinafter referred to by the name 'Antong Two'.

The new *Hibiscus* is a naturally-occurring branch mutation of an unnamed selection of *Hibiscus syriacus*, not patented. The cultivar Antong Two was discovered and selected by the Inventor within a population of plants of the parent selection in a controlled environment in Andong Provence, South Korea in 1995.

Asexual reproduction of the new *Hibiscus* by softwood cuttings in a controlled environment in Seoul, South Korea since 1996, has shown that the unique features of this new *Hibiscus* are stable and reproduced true to type in successive generations.

SUMMARY OF THE INVENTION

The cultivar Antong Two has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Antong Two'. These characteristics in combination distinguish 'Antong Two' as a new and distinct cultivar of *Hibiscus*:

1. Compact, upright and outwardly spreading plant habit.
2. Freely branching habit.
3. Dark green-colored leaves.
4. Small long-lasting white-colored flowers with red purple-colored centers and venation.
5. Good garden performance.

Plants of the new *Hibiscus* can be compared to plants of the parent selection. Plants of the new *Hibiscus* differ primarily from plants of the parent selection in plant size as plants of the new *Hibiscus* are more compact than plants of the parent selection.

Plants of the new *Hibiscus* can be compared to plants of the *Hibiscus syriacus* cultivar Red Heart, not patented. In side-by-side comparisons conducted in Grand Haven, Mich., plants of the new *Hibiscus* differed from plants of the cultivar Red Heart in the following characteristics:

1. Plants of the new *Hibiscus* were more compact and less vigorous than plants of the cultivar Red Heart.
2. Plants of the new *Hibiscus* had darker green-colored leaves than plants of the cultivar Red Heart.
3. Plants of the new *Hibiscus* had smaller flowers than plants of the cultivar Red Heart.
4. Flowers of plants of the new *hibiscus* lasted longer than flowers of plants of thr cultivar Red Heart.
5. Plants of the new *Hibiscus* had smaller sepals than plants of the cultivar Red Heart.
6. Plants of the new *Hibiscus* had shorter peduncles than plants of the cultivar Red Heart.

BRIEF DESCRIPTION OF THE PHOTOGRAPHS

The accompanying colored photographs illustrate the overall appearance of the new *Hibiscus*, showing the colors as true as it is reasonably possible to obtain in colored reproductions of this type. Colors in the photographs may differ slightly from the color values cited in the detailed botanical description which accurately describe the colors of the new *Hibiscus*.

The photograph at the top of the sheet is a close-up view of a typical flower of 'Antong Two'.

The photograph at the bottom of the sheet comprises a side perspective view of typical flowering plants of 'Antong Two' grown in an outdoor nursery.

DETAILED BOTANICAL DESCRIPTION

The aforementioned photographs and following observations, measurements and values describe plants grown in Grand Haven, Mich. during the summer in a polypropylene-covered shadehouse and under conditions which closely approximate commercial production. Plants were about three years old when the photographs and the description were taken. In the description, color references are made to The Royal Horticultural Society Colour Chart, 1995 Edition, except where general terms of ordinary dictionary significance are used.

Botanical classification: *Hibiscus syriacus* cultivar Antong Two.

Parentage: Naturally-occurring branch mutation of an unnamed selection of *Hibiscus syriacus*, not patented.

Propagation:

*Type*.—By vegetative terminal cuttings.

*Time to initiate roots*.—About 20 days at 24° C.

*Time to develop roots*.—About three months at 24° C.

*Root description*.—Fibrous.

*Rooting habit*.—Freely branching.

Plant description:

*Plant form and growth habit*.—Perennial shrub. Compact, upright and somewhat outwardly spreading plant habit. Moderately vigorous growth habit.

*Branching habit*.—Freely branching, usually about 24 lateral branches develop per plant after pinching (removal of terminal) apex).

*Plant height*.—About 82 cm.

*Plant diameter* (*area of spread*).—About 65 cm.

Lateral branch description:

*Length*.—About 32 cm.

*Diameter*.—About 6 mm.

*Internode length*.—About 4 cm.

*Texture, immature*.—Smooth, glabrous.

*Texture, mature*.—Woody.

*Color, immature*.—147A.

*Color, mature*.—191B.

Foliage description:

*Arrangement*.—Alternate, simple.

*Length*.—About 7.5 cm.

*Width*.—About 4 cm.

*Shape*.—Ovate to lanceolate.

*Apex*.—Acute.

*Base*.—Cuneate.

*Margin*.—Crenate; undulate.

*Texture, upper and lower surfaces*. —Smooth, glabrous; rugose.

*Venation pattern*.—Palmate; reticulate.

*Color*.—Developing foliage, upper surface: 143A. Developing foliage, lower surface: 143B. Mature foliage, upper surface: 136A; venation, 136A. Mature foliage, lower surface: 146A; venation, 146A.

*Petiole*.—Length: About 7 cm. Diameter: About 2 mm. Texture, upper and lower surfaces: Smooth, glabrous. Color, upper surface: 136A. Color, lower surface: 146A.

Flower description:

*Flower appearance/arrangement*.—Single rotate flowers; terminal and axillary. Freely flowering habit with usually about 22 flowers developing per lateral branch. Flowers face upright to outwardly.

*Flower longevity*.—Flowers are long lasting, lasting for about three days on the plant. Flowers not persistent.

*Natural flowering season*.—Typically July and August in Michigan.

*Flower diameter*.—About 9 cm.

*Flower length* (*height*).—About 4.5 cm.

*Flower bud*.—Length: About 2 cm. Diameter: About 1 cm. Shape: Ovate. Color: 147B.

*Petals*.—Arrangement: Corolla consists of a single whorl of five petals. Length: About 2 cm. Width: About 2 cm to 3.5 cm. Shape: Obovate. Apex: Rounded. Base. Attenuate. Margin: Entire. Texture, upper and lower surfaces; Smooth, glabrous. Color: When opening and fully opened, upper surface: Close to 155D; towards the base and venation, 60A. Color becoming closer to 155A with development. When opening and fully opened, lower surface: Close to 155D.

*Sepals*.—Appearance: Five sepals fused into a tubular calyx. Length: About 6 mm. Width: About 6 mm. Shape: Roughly rhombic. Apex: Acute. Margin: Entire. Texture, upper and lower surfaces: Smooth, glabrous. Color, immature and mature, upper surface: 147C. Color, immature and mature, lower surface: 147B.

*Peduncles*.—Length: About 8 mm. Diameter: About 3 mm. Strength: Strong, flexible. Texture: Smooth, glabrous. Color: 147B.

*Reproductive organs*.—Androecium: Anther shape: Rounded to oblong. Anther length: About 2 mm. Anther color: Close to 155D. Amount of pollen: Abundant. Pollen color: Close to 158B. Gynoecium: Pistil length: About 3.6 mm. Style length: About 3.3 cm. Style color: Close to 155D. Stigma appearance: Five, rounded. Stigma color: 158B. Ovary color: Close to 155D.

*Seeds*.—Quantity per flower: About 20. Length: About 6 mm. Diameter: About 4 mm. Color: 192A.

Garden performance: Plants of the new *Hibiscus* have been observed to have excellent garden performance and to tolerate rain, wind and temperatures ranging from about −29° C. to about 38° C.

Pathogen/pest resistance: Plants of the new *Hibiscus* have not been shown to be resistant to pathogens and pests common to *Hibiscus*.

It is claimed:

1. A new and distinct *Hibiscus* plant named 'Antong Two' as illustrated and described.

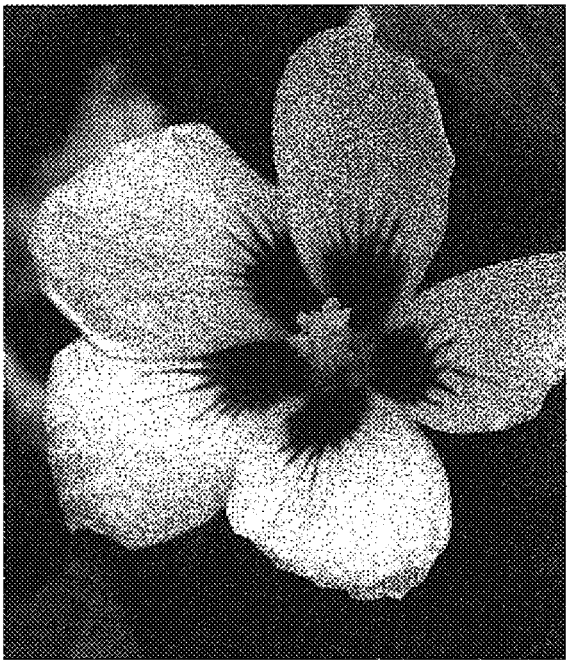
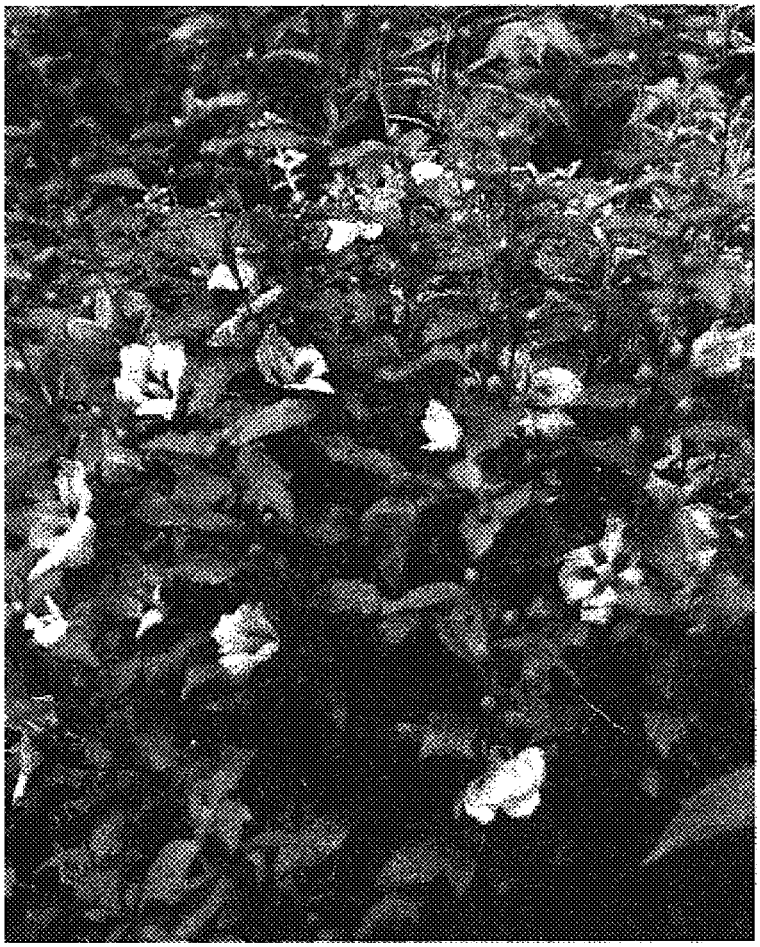

* * * * *